(12) United States Patent
Nunn et al.

(10) Patent No.: US 9,827,339 B2
(45) Date of Patent: Nov. 28, 2017

(54) METHOD AND APPARATUS UTILIZING UV-A AND UV-C FOR TREATMENT OF TEXTILE MATERIALS

(71) Applicant: PSIL HOLDINGS LLC, Tulsa, OK (US)

(72) Inventors: Kayren Joy Nunn, Bixby, OK (US); Susan Hughes Brown, Bixby, OK (US); Steven Jacob Brown, Bixby, OK (US)

( * ) Notice: Subject to any disclaimer, the term of this patent is extended or adjusted under 35 U.S.C. 154(b) by 0 days.

(21) Appl. No.: 14/672,139

(22) Filed: Mar. 28, 2015

(65) Prior Publication Data

US 2017/0014537 A1   Jan. 19, 2017

(51) Int. Cl.
| | |
|---|---|
| *A61L 2/00* | (2006.01) |
| *A61L 2/10* | (2006.01) |
| *A61L 2/24* | (2006.01) |
| *D06M 10/00* | (2006.01) |

(52) U.S. Cl.
CPC ...... *A61L 2/10* (2013.01); *A61L 2/24* (2013.01); *D06M 10/001* (2013.01); *A61L 2202/11* (2013.01); *A61L 2202/26* (2013.01)

(58) Field of Classification Search
CPC ........... A61L 2/10; A61L 2/24; D06M 10/001

USPC .......................................................... 422/24
See application file for complete search history.

(56) References Cited

U.S. PATENT DOCUMENTS

2010/0102253 A1* 4/2010 Chang .................... A47L 23/00
250/492.1

\* cited by examiner

*Primary Examiner* — Kevin Joyner

(57) ABSTRACT

The present invention discloses a method and corresponding apparatus utilizing UV-A and UV-C for treatment of textile materials. The method comprises the steps of (a) exposing incoming textile materials to UV-A radiation for detection of optically brightened textile materials and/or synthetic fiber materials; (b) separating detected optically brightened textile materials and/or synthetic fiber materials from the incoming textile materials; (c) exposing the separated incoming textile materials to UV-C radiation for sterilization and surface modification of the textile materials to increase wettability and absorbability and reduce pilling. The apparatus comprises an enclosed segregation chamber disposed with a cascading conveying means, a UV-A radiation source and an optically brightened textile materials and/or synthetic fiber materials separating means therewithin, and an enclosed segregation chamber disposed with a UV-C radiation source therewithin.

8 Claims, 2 Drawing Sheets

US 9,827,339 B2

METHOD AND APPARATUS UTILIZING UV-A AND UV-C FOR TREATMENT OF TEXTILE MATERIALS

BACKGROUND

The present invention is generally in the field of equipment to support the "Method and System of Processing Waste Fabric to Rejuvenate Fibrous Materials" for the recycling of post industrial and pre consumer materials. In particular, the field of this invention relates to a method and apparatus for utilizing UV-A and UV-C for treatment of textile materials.

SUMMARY

The recycling industry has historically considered all textile waste material to be peripheral, relegating it to be swept from cutting tables and mill floors and deposited in bins or baled along with any foreign debris mingled with it. If the scrap were recycled, all of the now indigenous debris would be recycled with it and therefore included in downcycled products where quality criteria are not strictly adhered to.

About half of the world's wastewater problems are linked to the production of textile goods, and many of the chemicals used to dye and finish fabrics are known to harm human health. Often clippings from carpet or fabric mills are replete with dangerous chemicals and are handled like toxic waste. Ironically, many of the products made from these materials are considered safe for use in the home. Since the beginning of the 21st century environmental concerns have become central to the global populace and designers in many fields have begun to reconsider their role in the production and consumption of consumer goods. The design community has concluded that without the utilization of sustainable fibers which are equal in quality and price to those of virgin, the global impact will remain negligible without exception. As designers embrace new technologies and materials, they must address the ecological impact of their designs in order to shape a more sustainable future. The 21st century has marked the beginning of a new textile revolution as it is becoming intelligent, sustainable and ethical to find solutions to this global waste crisis. The method and processes for producing high quality rejuvenated textile waste fibers is dependent upon critical data as well as specialty equipment and technologies. This amalgamation of this approach becomes evident in the establishment of a rejuvenation process based upon both intuitive and scientific analysis of data. Furthermore, quality control systems have been instituted which are singular within the industry, as well as unique chemistry and engineered equipment which gently, not aggressively, deconstruct fabrics reverting them to yarn segments (Pre-Fiberization) and ultimately to individual fibers (Fiber Refinement). Fiber Rejuvenation is a holistic system and, if approached in this manner, can transform what is now a "niche" downcycled market for apparel and industrial textiles into a mainstream sustainable raw material that is equal in quality and costs less than virgin raw material and creates value to the industry and its consumers. It is in this that we find the need to use technology and science to segregate families of fibers and to purify those fibers so that they can be competitive with their virgin counterparts while rendering a realistic sustainable solution both for the environment, our consumers, and business.

DETAILED DESCRIPTION

Figure 1:
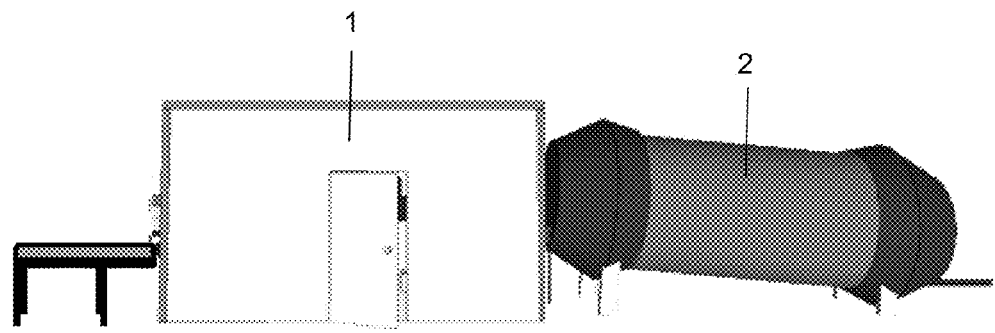
FIG. 1 illustrates a view of an embodiment of the present invention.

It is an object of the present invention to provide a method and apparatus utilizing UV-A and UV-C for treatment of textile materials, so that optically brightened textile materials are segregated from non-optically brightened textile materials for subsequent textile processing. It is also an object of the present invention to provide a method and apparatus utilizing UV-A and UV-C for treatment of textile materials, so that synthetic fabrics or fibers can be separated from natural fibers.

It is another object of the present invention to provide a method and apparatus utilizing UV-A and UV-C for treatment of textile materials, so that the textile materials are sterilized to rid the materials of system-related bacteria or human contamination for subsequent textile processing.

It is another object of the present invention to provide a method and apparatus utilizing UV-A and UV-C for treatment of textile materials, so that the surface of the textile materials is modified to increase the wettability and absorbability.

It is yet another object of the present invention to provide a method and apparatus utilizing UV-A and UV-C for treatment of textile materials, so that the surface of the textile materials is modified to eliminate pilling issues that create neps in the rejuvenation of natural fibers.

To attain this, the present invention provides a method utilizing UV-A and UV-C for treatment of textile materials, comprising the steps of:

(a) exposing incoming textile materials to UV-A radiation for detection of optically brightened textile materials and/or synthetic fiber materials;

(b) separating detected optically brightened textile materials and/or synthetic fiber materials from the incoming textile materials;

(c) exposing the separated incoming textile materials to UV-C radiation for sterilization and surface modification of the textile materials to increase wettability and absorbability and reduce pilling.

In step (a), the UV-A radiation has a wavelength between 315 nanometers and 400 nanometers. The incoming textile materials traverse on a cascading conveying means which operates to flip and turn the incoming textile materials with minimal human contact as the incoming textile materials are exposed to UV-A radiation. The incoming textile materials are presented on the conveyor in form of one single layer.

Step (b) is manually operated, in which one or more human operators wearing protective gear separates the detected optically brightened textile materials and/or synthetic fiber materials from the incoming textile materials.

The UV-C radiation in step (c) has a wavelength between 100 nanometers and 280 nanometers.

The present invention also provides an apparatus utilizing UV-A and UV-C for treatment of textile materials, comprising:

an enclosed segregation chamber having an input end and an output end which receives incoming textile materials from the input end and separates optically brightened textile materials and/or synthetic fiber materials from the incoming textile materials;

a cascading conveying means disposed within the segregation chamber which traverses the incoming textile materials from the input end to the output end and operates to flip and turn the incoming textile materials with minimal human contact;

a UV-A radiation source disposed within the segregation chamber which irradiates the cascading conveying means with UV-A radiation for detection of optically brightened textile materials and/or synthetic fiber materials;

the cascading conveying means defines a manual separating station whereat detected optically brightened textile materials and/or synthetic fiber materials are removed from the cascading conveying means;

an enclosed sterilization chamber which receives textile materials output from the segregation chamber; and a UV-C radiation source disposed within the sterilization chamber which irradiates the sterilization chamber with UV-C radiation for sterilization and surface modification of the textile materials to increase wettability, absorbability and reduce pilling.

The cascading conveying means comprises a plurality of conveyor belts arranged in a cascade manner, wherein each of the conveyor belts has an outlet end, and the conveyor belt lower down projects forwardly of the outlet end of the conveyor belt thereabove. The conveyor belt may for example be 6 foot long by 3 foot wide.

The plurality of conveyor belts comprises a first conveyor belt which connects the input end of the segregation chamber to a subsequent conveyor belt, and the first conveyor belt is slantedly disposed so that the incoming textile materials traverse upward from the input end of the segregation chamber, which is at a lower position, to the subsequent conveyor belt, which is at an upper position.

The segregation chamber is disposed with air ventilation and filtration means to remove fine dust particles from the air in the segregation chamber.

The UV-A radiation source is disposed on top of the cascading conveying means. The UV-A radiation source delivers UV-A radiation with a wavelength between 315 nanometers and 400 nanometers.

An optically brightened textile materials and/or synthetic fiber materials separating means is disposed within the segregation chamber and coupled to an area external to the segregation chamber, whereby detected optically brightened textile materials and/or synthetic fiber materials are removed from the segregation chamber. The optically brightened textile materials and/or synthetic fiber materials separating means is a vacuum area wherein the detected optically brightened textile materials are transported to the area external to the segregation chamber by negative pressure.

The detected optically brightened textile materials and/or synthetic fiber materials are manually removed from the segregation chamber.

The sterilization chamber is in form of a rotating cylinder having an input end and an output end, wherein the textile materials traverse from the input end to the output end as they are irradiated by the UV-C radiation source.

The rotating cylinder is approximately 1-2 meters in diameter and 3-5 meters long, and it is mounted on a stand with an effective slope of −0.12 to −0.16. It has an interior surface which is highly reflective.

The UV-C radiation source delivers UV-C radiation with a wavelength between 100 nanometers and 280 nanometers. The UV-C radiation source is preferably a pulsating UV-C light source as it consumes less energy during operation. Alternatively, the UV-C radiation source could also be a constant UV-C light source.

The interior surface of the rotating cylinder is disposed with a plurality of rows of opening slats which are angled with a travel axis along which the fabric pieces travel in the rotating cylinder, and the rows are offset from each other. The opening slats are made of highly reflective material.

Referring to the drawings in detail,

FIG. 1 illustrates the structure of the apparatus of an embodiment of the present invention.

Figure 2:
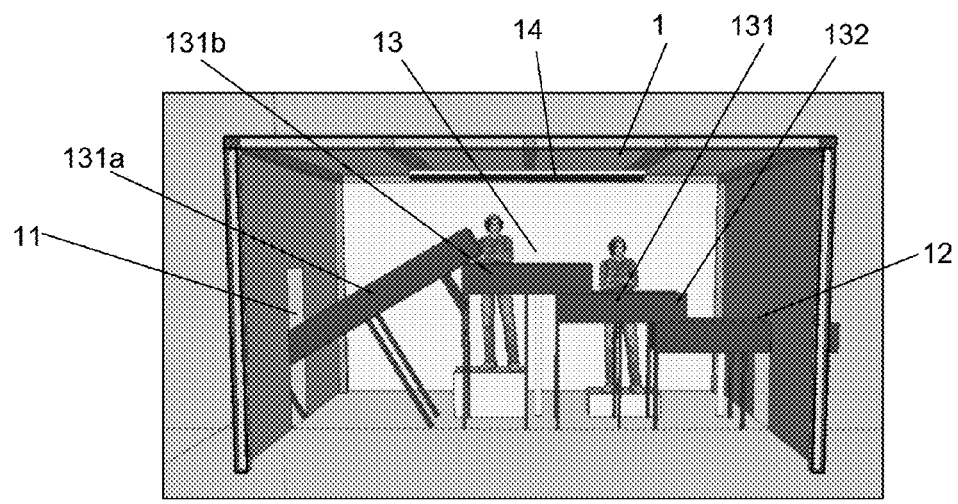
FIG. 2 illustrates a view of an embodiment of the segregation chamber.

FIG. 2 illustrates the structure of the segregation chamber of the apparatus of an embodiment of the present invention.

Figure 3:
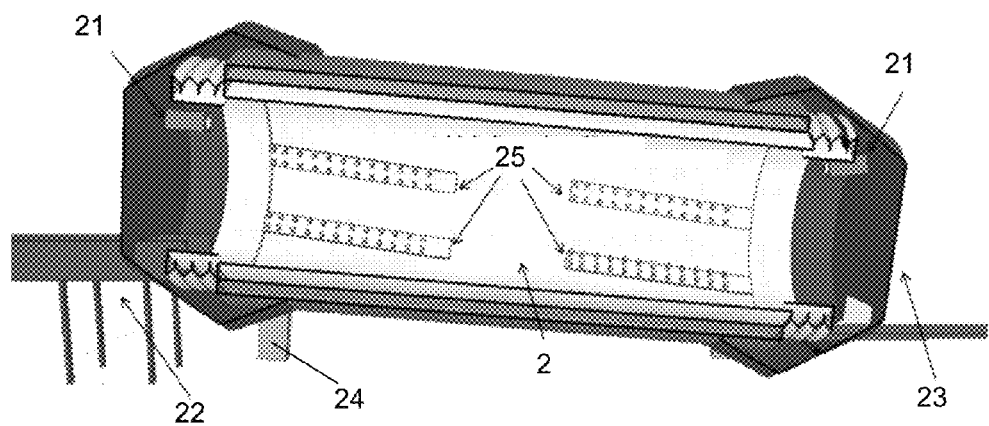
FIG. 3 illustrates a view of an embodiment of the sterilization chamber.

FIG. 3 illustrates the structure of the sterilization chamber of the apparatus of an embodiment of the present invention.

The present invention provides a method utilizing UV-A and UV-C for treatment of textile materials, comprising the steps of:

(a) exposing incoming textile materials to UV-A radiation for detection of optically brightened textile materials and/or synthetic fiber materials;

(b) separating detected optically brightened textile materials and/or synthetic fiber materials from the incoming textile materials;

(c) exposing the separated incoming textile materials to UV-C radiation for sterilization and surface modification of the textile materials to increase wettability and absorbability and reduce pilling.

Step (a) utilizes UV-A radiation for detection of optically brightened textile materials. The Optical Brightening Agents known as OBA; or Fluorescent Whitening Agents, known as FWA or other UV type treatments, are the agents that are used to treat fabrics and yarns and are detectable in UV-A environment.

UV-A may also be used to segregate synthetics such as Polyester, Nylon, Rayon, etc. from natural fabrics or yarn segments such as Flax, Linen, Hemp, Sunn Hemp, Jute, Ramie, Kenaf, Straw, Banana, Pineapple, Papyrus, Alfagras/Esparto, Alginate, Urena/Congo Jute, Nettle, Raffia, etc. These synthetic fibers could be treated with UV treatments which would make them detectable to UV light, but in their natural state they are not fluorescent. As a general rule, synthetic fibers manufactured since World War Two contain fluorescents, unless for a specific purpose otherwise manufactured. These synthetic fibers would be classified as Polyesters, also known as PET. Examples of fibers within this group include the following:

Poly Cyclohexane-Dimethanol Terephthalate (PCT)
Polytrimethylene Terephthalate (PTT)
Polybutylene Terephthalate (PBT)
Polyolefines: Polypropylene (PP) and Polyethylene (PE)
Polyurethanes (PU): Polyuretherthane (PUR), Elasthane (EL), Elastodiene (ED)
Co-Polymers: ModAcrylics (MAC), also known as Acrylics, and similar fibers
Fluro Fibers: Polytertafluorethylene (PTFE), Ethylene Chlorotrifluorethylene (ECTFE), Polyvinyl Fluoride (PVF), etc.
Polyamides: Nylon (Polyamide 4.6, Polyamide 6, Polyamide 6.6, Polyamide 6.12, Polyamide 11, etc.)
Polymer fibers from natural derivatives such as plant or proteins: Rayon or Viscose (CV), Bamboo Regenerated (CBAM), Modal (CMD), Lyocell (CLY), Seaweed Lyocell (CLYS), Acetate (CA), Tri-Acetate (CTA), Peanut (PEA), Corn (COR), Soybean (SPF), Alginate (ALG), Casein (CS), Milk (CS), Polylactic Acid (PLA), etc.
Other Synthetics: Meta-Aramid (m-AR), Para-Aramid (p-AR), Melamine Formaldehyde (MF), Polybenzimidazole (PBI), Polycarbonate (PC), Polyetheretherketone (PEEK), Polyether-Imide (PEI), Polyetherketone (PEK), Polyethersulfone (PES), Polyethyleneaphtalate (PEN), Polyimide (PI), Polymethy Methacrylate (PMMA), Polyoxymethylene or Polyacetal (POM), Polyphenelene Oxide (PPO), Polyphenylenesulfide (PPS), Polystyrene (PS), Polysulfone (PSU), Liquid Crystal Polymer (LCP), etc.

Thus the utilization of UV-A at step (a) assures excellent quality control for these specific qualifications.

In step (a), the UV-A radiation has a wavelength between 315 nanometers and 400 nanometers. The incoming textile materials traverse on a cascading conveying means which operates to flip and turn the incoming textile materials with minimal human contact as the incoming textile materials are exposed to UV-A radiation. The incoming textile materials are presented on the conveyor in form of one single layer. This allows all sides of the textile materials to be exposed to UV-A radiation. Once the UV-A radiation exposes the optically brightened textile materials and/or synthetic fiber materials, one or more human operators wearing protective gear separates the detected optically brightened textile materials and/or synthetic fiber materials from the incoming textile materials in step (b).

In step (c), the separated incoming textile materials are exposed to UV-C radiation to accomplish the following in relation to the rejuvenation of textile materials:

(1) to pre-sterilize the fabric pieces or fiber in order to rid the materials of bacteria associated with the system or human contamination;

(2) to modify the surface of the fabric pieces or fiber in order to increase their wettability and absorbability for the purpose of downstream production or products; and (3) to modify the surface of the fabric pieces or fiber in order to eliminate the pilling issues that create neps in the rejuvenation of natural fibers.

In this step, the UV-C radiation penetrates the entirety of the textile materials in order to optimize pre-sterilization. Pre-sterilization of the textile materials is important to ensuring quality materials for a number of downstream applications created from rejuvenated textile materials. Applications such as pharmaceutical, medical, baby, cosmetic, or food grade products require levels of microbial testing of the textile materials prior to downstream non-woven or textile processing. This is the initial area where the removal of those microbes will occur. Utilizing UV-C is a powerful step when used in conjunction with this methodological approach. Exposing the textile materials to the UV-C radiation can rid the materials of bacteria associated with the earlier stages of processing and the human contamination that has occurred upstream. The UV-C radiation is typically applied at a wavelength between 100 nm and 280 nm for this type of disinfection. This is yet another critical step in assuring a quality rejuvenated fiber in downstream applications.

The exposure of textile materials to UV-C radiation in step (c) also has an effect on the preparedness of the textile materials throughout the remainder of the rejuvenation process. While the UV-C radiation is sterilizing the textile materials, it is also modifying the surface of the textile materials to create greater hydrophobicity. Due to the modification of the surface of the textile materials, nep counts are reduced in the rejuvenation of the cotton fibers. Pilling is significantly reduced when rejuvenating synthetic fibers due to the same surface modification. The below table shows the results of tests conducted according to ASTM C5866-12.

| Cotton | Pre UV-C Treatment | Post-UV-C Treatment/Fiber | Post UVC Treatment in Yarn Application |
|---|---|---|---|
| Test 1 | 870 neps/gram | 430 neps/gram | 60 neps/gram |
| Test 2 | 1100 neps/gram | 480 neps/gram | 72 neps/gram |
| Test 3 | 1286 neps/gram | 760 neps/gram | 73 neps/gram |

Tests above were performed on a High Speed Fibre Testing Unit, AFIS to determine nep count in the rejuvenated cotton fibers which uses a sliver of cotton fed into the automated unit to determine how many neps per gram of fiber that was detected.

The UV irradiation of the textile materials also affects the color strength of the textile materials. Previous studies show that UV-C irradiation adds value to coloration and also increases the dye uptake ability of cotton fabrics through oxidation of surface fibers of cellulose. UV or gamma are ionizing radiations that interact with the material by colliding with the electrons in the shells of atoms. They slowly lose their energy in material and are able to travel significant distances before stopping. The free radicals formed are extremely reactive, and they will combine with the material in their vicinity. Upon irradiation, the cross linking changes the crystal structure of the cellulose, which can add value in the coloration process and causes photo modification of surface fibers. The irradiated modified fabrics allow an increase in the wettability of hydrophobic fibers, which improves the uptake of organic process chemicals used to eradicate surface chemicals in the next process of rejuvenation. It also has a positive effect in improving the uptake of the dyestuffs and will increase the depth of shade in downstream printing and dyeing.

As illustrated in the accompanying drawings, the present invention also provides an apparatus for implementing the aforementioned method utilizing UV-A and UV-C for treatment of textile materials. The apparatus comprises an enclosed segregation chamber 1 and an enclosed sterilization chamber 2. The segregation chamber 1 has an input end 11 and an output end 12 which receives incoming textile materials from the input end 11 and separates optically brightened textile materials and/or synthetic fiber materials from the incoming textile materials. A cascading conveying means 13 and a UV-A radiation source 14 are disposed within the segregation chamber 1. The cascading conveying means 13 traverses the incoming textile materials from the input end 11 to the output end 12 of the segregation chamber 1 and operates to flip and turn the incoming textile materials with minimal human contact. The cascading conveying means 13 defines a manual separating station whereat detected optically brightened textile materials and/or synthetic fiber materials are removed from the cascading conveying means 13. The cascading conveying means 13 comprises a plurality of conveyor belts 131 arranged in a cascade manner, wherein each of the conveyor belts 131 has an outlet end 132, and the conveyor belt 131 lower down projects forwardly of the outlet end 132 of the conveyor belt 131 thereabove. The conveyor belt 131 may for example be 6 foot long by 3 foot wide, but it could be shorter or longer depending on the production rate needed of the production line. The plurality of conveyor belts 131 comprises a first conveyor belt 131*a* which connects the input end 11 of the segregation chamber 1 to a subsequent conveyor belt 131*b*, and the first conveyor belt 131*a* is slantedly disposed so that the incoming textile materials traverse upward from the input end 11 of the segregation chamber 1, which is at a lower position, to the subsequent conveyor belt 131b, which is at an upper position.

The UV-A radiation source 14 irradiates the cascading conveying means 13 with UV-A radiation for detection of optically brightened textile materials and/or synthetic fiber materials. It is disposed on top of the cascading conveying means 13 and delivers UV-A radiation with a wavelength between 315 nanometers and 400 nanometers.

In other embodiment, an optically brightened textile materials and/or synthetic fiber materials separating means may be disposed within the segregation chamber 1 and coupled to an area external to the segregation chamber 1, whereby detected optically brightened textile materials and/or synthetic fiber materials are removed from the segregation chamber 1. The optically brightened textile materials and/or synthetic fiber materials separating means is a vacuum area wherein the detected optically brightened textile materials and/or synthetic fiber materials are transported to the area external to the segregation chamber 1 by negative pressure. The detected optically brightened textile materials and/or synthetic fiber materials are manually removed from the segregation chamber 1.

The segregation chamber 1 is also disposed with air ventilation and filtration means (not shown) to remove fine dust particles from the air in the segregation chamber.

The sterilization chamber 2 receives textile materials output from the segregation chamber 1, and is disposed with a UV-C radiation source 21 therewithin. The UV-C radiation source 21 irradiates the sterilization chamber 2 with UV-C radiation for sterilization and surface modification of the textile materials to increase wettability, absorbability and reduce pilling. The UV-C radiation source 21 delivers UV-C radiation with a wavelength between 100 nanometers and 280 nanometers, and is a pulsating UV-C light source.

The sterilization chamber 2 is in form of a rotating cylinder having an input end 22 and an output end 23, wherein the textile materials traverse from the input end 22 to the output end 23 as they are irradiated by the UV-C radiation source 21. The rotating cylinder is approximately 1-2 meters in diameter and 3-5 meters long, and it is mounted on a stand 24 with an effective slope of −0.12 to −0.16. It has an interior surface which is highly reflective. The interior surface of the rotating cylinder is disposed with a plurality of rows of opening slats 25 which are angled with a travel axis along which the fabric pieces travel in the rotating cylinder, and the rows are offset from each other. The opening slats 25 are made of highly reflective material, and they assist in the opening or "unfolding" of the textile materials while the materials are being tumbled in the rotating cylinder. According to the above disclosure, a person skilled in the art may make suitable modifications and changes to the above embodiments. Therefore, the present invention is not limited by the above disclosure and the embodiment described. Modifications and changes to the present invention should fall within the scope of the present invention as defined by the claims. Besides, although certain technical terms have been used throughout the specification, the technical terms are intended for ease of explanation and are not intended to restrict the present invention in any ways.

The invention claimed is:

1. A method utilizing UV-A and UV-C for treatment of textile materials and/or synthetic fiber materials, comprising the steps of:
    (a) exposing incoming textile materials and/or synthetic fiber materials to UV-A radiation for detection of optically brightened textile materials and/or synthetic fiber materials;
    (b) separating detected optically brightened textile materials and/or synthetic fiber materials from the incoming textile materials;
    (c) exposing the separated incoming textile materials and/or synthetic fiber materials to UV-C radiation.

2. The method of claim 1, wherein step (b) is manually operated, in which one or more human operators wearing protective gear separates the detected optically brightened textile materials and/or synthetic fiber materials from the incoming textile materials.

3. The method of claim 1, wherein the UV-A radiation in step (a) has a wavelength between 315 nanometers and 400 nanometers.

4. The method of claim 1, wherein the incoming textile materials and/or synthetic fiber materials traverse on a cascading conveying means which operates to flip and turn the incoming textile materials and/or synthetic fiber materials with minimal human contact in step (a) as the incoming textile materials and/or synthetic fiber materials are exposed to UV-A radiation; and the incoming textile materials and/or synthetic fiber materials are presented to the conveyor in form of one single layer.

5. The method of claim 1, wherein the UV-C radiation in step (c) has a wavelength between 100 nanometers and 280 nanometers.

6. The method of claim 1, wherein the exposure to UV-C radiation is sufficient to sterilize the textile materials and/or synthetic fiber materials.

7. The method of claim 1, wherein the exposure to UV-C radiation is sufficient to modify the surface of the textile materials and/or synthetic fiber materials.

8. The method of claim 7, wherein modification of the surface of the textile materials and/or synthetic fiber materials increases their wettability, increases their absorbability, and/or reduces pilling.

\* \* \* \* \*